United States Patent
Liu et al.

(10) Patent No.: US 9,458,330 B2
(45) Date of Patent: Oct. 4, 2016

(54) METHOD OF PREPARING CARBON-COATED MANGANOUS OXIDE AND CARBON-COATED MANGANOUS OXIDE PREPARED USING THE METHOD

(71) Applicant: Jianhong Liu, Shenzhen (CN)

(72) Inventors: Jianhong Liu, Shenzhen (CN); Qianling Zhang, Shenzhen (CN); Chuanxin He, Shenzhen (CN); Chuhong Liao, Shenzhen (CN)

(73) Assignee: SHENZHEN EIGEN-EQUATION GRAPHENE TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 14/946,800

(22) Filed: Nov. 20, 2015

(65) Prior Publication Data

US 2016/0145445 A1  May 26, 2016

(30) Foreign Application Priority Data

Nov. 20, 2014 (CN) .......................... 2014 1 0666514

(51) Int. Cl.
| | |
|---|---|
| *C09D 5/16* | (2006.01) |
| *B05D 1/18* | (2006.01) |
| *B05D 3/02* | (2006.01) |
| *B05D 3/00* | (2006.01) |

(52) U.S. Cl.
CPC .............. *C09D 5/1618* (2013.01); *B05D 1/18* (2013.01); *B05D 3/007* (2013.01); *B05D 3/0272* (2013.01)

(58) Field of Classification Search
CPC ........... C01G 45/02; C09C 1/00; C09C 3/08; C09C 3/10; C09D 5/1618; B05D 3/607; B05D 3/0272; B05D 1/18
See application file for complete search history.

(56) References Cited

PUBLICATIONS

Derwent-Acc-No. 2013-Q42534, abstract of Chinese Patent Specification No. CN 103094551 (May 2013).*
Derwent-Acc-No. 2013-V71703, abstract of Chinese Patent Specification No. CN 103311529 (Sep. 2013).*
Derwent-Acc-No. 2014-H16260, abstract of Chinese Patent Specification No. CN 103606654 (Feb. 2014).*

* cited by examiner

*Primary Examiner* — Anthony J Green
(74) *Attorney, Agent, or Firm* — Matthias Scholl P.C.; Matthias Scholl

(57) ABSTRACT

A method of preparing carbon-coated manganous oxide, the method including: (1) preparing a liquid polyacrylonitrile (LPAN) solution as a carbon source, stirring the LPAN solution at between 100 and 200° C. to yield a cyclized polyacrylonitrile solution; (2) heating the cyclized LPAN solution at between 200 and 300° C. to yield a thermally-oxidized polyacrylonitrile (OPAN) having a ladder structure; (3) mixing the thermally-oxidized polyacrylonitrile with a manganese compound, to yield a mixture, and adding a solvent to the mixture, uniformly mixing, to yield a polyacrylonitrile coated manganese compound; (4) drying the polyacrylonitrile coated manganese compound until the solvent is evaporated completely and the polyacrylonitrile coated on the manganese compound is crosslinked to form a solid, to yield a carbonized precursor coated manganese compound; and (5) calcining the carbonized precursor coated manganese compound in the presence of an inert gas flow, to yield a carbon-coated manganous oxide.

9 Claims, 4 Drawing Sheets

METHOD OF PREPARING CARBON-COATED MANGANOUS OXIDE AND CARBON-COATED MANGANOUS OXIDE PREPARED USING THE METHOD

CROSS-REFERENCE TO RELATED APPLICATIONS

Pursuant to 35 U.S.C. §119 and the Paris Convention Treaty, this application claims the benefit of Chinese Patent Application No. 201410666514.0 filed Nov. 20, 2014, the contents of which are incorporated herein by reference.

BACKGROUND OF THE INVENTION

1. Field of the Invention

The invention relates to a method of preparing carbon-coated manganous oxide (MnO) as well as carbon-coated manganous oxide prepared using the method.

2. Description of the Related Art

Cuprous oxide is a common marine antifouling coating. However, copper compounds are toxic. Manganous oxide is cheap and abundant in the nature, so it is a promising substitute for cuprous oxide. However, manganous oxide is relatively unstable, which greatly limits its antifouling potential.

SUMMARY OF THE INVENTION

In view of the above-described problems, it is one objective of the invention to provide a method of preparing carbon-coated manganous oxide and carbon-coated manganous oxide prepared by the method. The prepared carbon-coated manganous oxide is stable at room temperature, and has a practicable release speed and long antifouling life.

To achieve the above objective, in accordance with one embodiment of the invention, there is provided a method of preparing carbon-coated manganous oxide, the method comprising:

(1) preparing a liquid polyacrylonitrile (LPAN) solution as a carbon source, stirring the LPAN solution at between 100 and 200° C. for between 100 and 200 hrs to yield a cyclized polyacrylonitrile solution;

(2) heating the cyclized LPAN solution at between 200 and 300° C. for between 1 and 10 hrs to yield a thermally-oxidized polyacrylonitrile (OPAN) comprising a ladder structure;

(3) mixing the thermally-oxidized polyacrylonitrile with a manganese compound with a mass ratio thereof being between 0.1:1 and 0.9:1, to yield a mixture, and adding a solvent to the mixture, uniformly mixing, to yield a polyacrylonitrile coated manganese compound;

(4) drying the polyacrylonitrile coated manganese compound in an oven at a temperature of between 200 and 250° C. for between 1 and 10 hrs until the solvent is evaporated completely and the polyacrylonitrile coated on the manganese compound is crosslinked to form a solid, to yield a carbonized precursor coated manganese compound; and (5) calcining the carbonized precursor coated manganese compound in the presence of an inert gas flow of between 10 and 500 mL/min for between 1 and 10 hrs at a temperature of between 500 and 900° C., to yield a carbon-coated manganous oxide.

In a class of this embodiment, in 1), a dopant is added to and uniformly mixed with the cyclized LPAN solution.

In a class of this embodiment, a mass ratio of the dopant to the LPAN solution is between 0.01:1 and 0.5:1.

In a class of this embodiment, the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, organometallic compound, or a mixture thereof; and the non-metallic dopant is silicon, phosphorus, boron, nitrogen, carbon, sulfur, or a compound thereof, or a mixture thereof.

In a class of this embodiment, the liquid polyacrylonitrile (LPAN) solution employs liquid polyacrylonitrile as a solute and contains no solvent, and the LPAN has a relative molecular weight of between 106 and 100000.

In a class of this embodiment, the PLAN is a homopolymer of acrylonitrile, or a copolymer of acrylonitrile and a vinyl monomer.

In a class of this embodiment, the vinyl monomer is selected from the group of styrene, methyl methacrylate, hydroxyethyl methylacrylate, acrylic acid, itaconic acid.

In a class of this embodiment, in 3), the uniform mixing of the mixture and the solvent is achieved by stirring, ultrasound, or ball milling.

In a class of this embodiment, in 3), the manganese compound is manganese dioxide ($MnO_2$) or a manganese salt.

In another aspect, the invention also provides a carbon-coated manganous oxide, which is prepared according to the mentioned-above method.

Advantages of the method of preparing carbon-coated manganous oxide are summarized as follows. The obtained carbon-coated manganous oxide has good compatibility with carbon source and the carbon membrane is porous, so that the release speed of manganous oxide can be effectively controlled, which is favorable for the carbon-coated manganous oxide to be used as an antifouling additive for marine antifouling paints. In addition, the outer coating of polyacrylonitrile can prevent the oxidation of manganous oxide, and the manganous oxide can be slowly released to the surface of the coating via the porous coating, which increases the contact area of the adsorbate and the catalyst, and improves the catalytic performance. The method of the invention involves a simple process and low production costs, and the resulting carbon-coated manganous oxide has high purity, high yield, uniform distribution of particle sizes, and good morphology. The LPAN solution contains multiple functional groups, and as a liquid precursor, after being modified using a dopant, the LPAN can uniformly mix with and bind to the dopant.

BRIEF DESCRIPTION OF THE DRAWINGS

The invention is described hereinbelow with reference to the accompanying drawings, in which.

DETAILED DESCRIPTION OF THE EMBODIMENTS

Figure 1A:
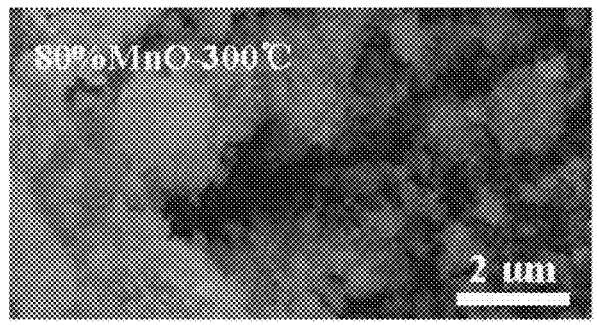
FIG. 1A is a SEM pattern of a product prepared in Example 1, where the product is prepared at a calcination temperature of 300° C.
Figure 1B:
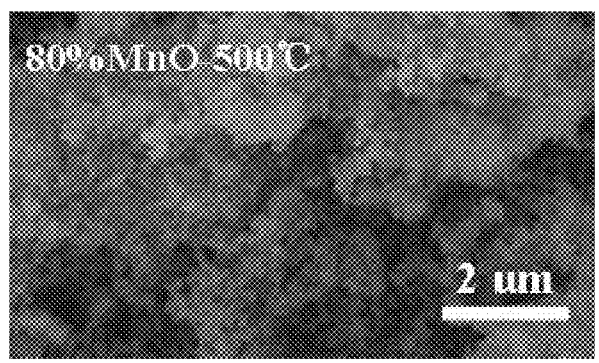
FIG. 1B is a SEM pattern of a product prepared in Example 1, where the product is prepared at a calcination temperature of 500° C.
Figure 1C:
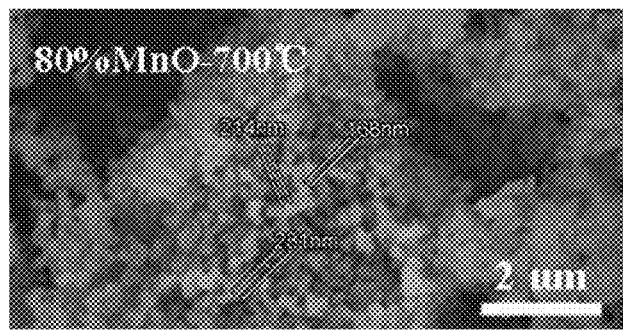
FIG. 1C is a SEM pattern of a product prepared in Example 1, where the product is prepared at a calcination temperature of 700° C.
Figure 1D:
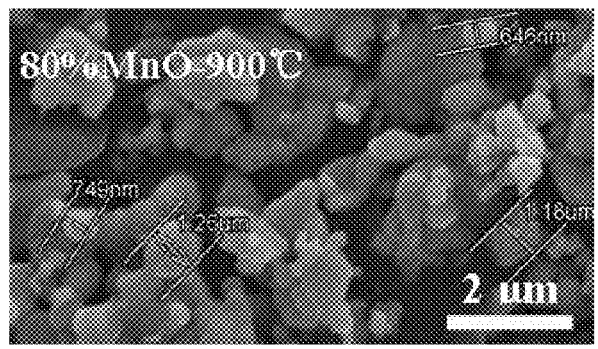
FIG. 1D is a SEM pattern of a product prepared in Example 1, where the product is prepared at a calcination temperature of 900° C.

For further illustrating the invention, experiments detailing a method of preparing a carbon-coated manganous oxide are described below. It should be noted that the following examples are intended to describe and not to limit the invention.

The carbon-coated manganous oxide resulting from solvent thermal treatment has good compatibility with carbon source and the carbon membrane is porous, so that the release speed of manganous oxide can be effectively controlled, which is favorable for the carbon-coated manganous oxide to be used as an antifouling additive for marine antifouling paints. In addition, the outer coating of polyacrylonitrile can prevent the oxidation of manganous oxide, and the manganous oxide can be slowly released to the surface of the coating via the porous coating, thereby increasing the contact area of the adsorbate and catalyst, and improving the catalytic performance.

The invention provides a method of preparing a carbon-coated manganous oxide, the method comprising:

(1) Preparing a liquid polyacrylonitrile (LPAN) solution as a carbon source, stirring the LPAN solution at between 100 and 200° C. for between 100 and 200 hrs to yield a cyclized polyacrylonitrile solution.

In (1), the liquid LPAN solution is stirred at the temperature of between 100 and 200° C. for between 100 and 200 hrs to yield the cyclized polyacrylonitrile solution. As a result, the linear LPAN molecule is transformed into a thermostable ladder structure, which can resist the pyrolysis during the high-temperature carbonization, thereby ensuring the high carbon residue rate and stable physicochemical properties. In the end, a carbon layer having a grapheme-like structure is formed.

The invention employs the PLAN instead of dilute PLAN as a carbon source and solute, and the liquid polyacrylonitrile has a relative molecular weight of between 106 and 100000, particularly, between 150 and 25000. The PLAN contains no solvent. The polymer is a long chain macromolecule with high molecular weight and high carbon content, and thus provides a structure base for the carbon coating.

Preferably, the LPAN is a homopolymer of acrylonitrile, or a copolymer of acrylonitrile and a vinyl monomer, and the vinyl monomer is selected from the group of styrene, methyl methacrylate, hydroxyethyl methylacrylate, acrylic acid, itaconic acid.

Preferably, the invention employs the self-made PLAN as a carbon source, and the former presents a liquid in the temperature of between minus 80° C. and 200° C., with a concentration of 0.8 and 1.2 g/cm$^2$. The polymer is a long chain macromolecule with high molecular weight and high carbon content, and thus provides a structure base for the carbon coating.

Preferably, in 1), a dopant is added to and uniformly mixed with the cyclized LPAN solution. The LPAN solution contains multiple functional groups, and as a liquid precursor, after being modified using a dopant, the LPAN can uniformly mix with and bind to the dopant.

As an improvement, in 1), a dopant is added to and uniformly mixed with the cyclized LPAN solution, and the mixing is achieved by stirring, ultrasound, or ball milling. The mass ratio of the dopant to the LPAN is between 0.01:1 and 0.5:1. The cyclized LPAN solution has multiple functional groups, which are adapted to tightly bind to the dopant or carbon material. Part of LPAN functional groups can coordinate with the dopant to achieve compatibility and coating in the molecular level. After grinding or stirring, the LPAN and the dopant are fully mixed and contacted. Preferably, the mixing is achieved by ball milling.

Preferably, the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, organometallic compound, or a mixture thereof; and the non-metallic dopant is silicon, phosphorus, boron, nitrogen, carbon, sulfur, or a compound thereof, or a mixture thereof. Preferably, the dopant is tin powder. The tin-doped PLAN has better stability, and tin powder can further improve the catalytic performance of carbon-coated manganous oxide.

(2) Heating the cyclized LPAN solution at between 200 and 300° C. for between 1 and 10 hrs to yield a thermally-oxidized polyacrylonitrile (OPAN) comprising a ladder structure.

Preferably, the heating time is 8 hours, so that the thermally-oxidized polyacrylonitrile has more stable chemical properties.

(3) Mixing the thermally-oxidized polyacrylonitrile with a manganese compound with a mass ratio thereof being between 0.1:1 and 0.9:1, to yield a mixture, and adding a solvent to the mixture, uniformly mixing, to yield a polyacrylonitrile coated manganese compound.

Preferably, the manganese compound is manganese dioxide ($MnO_2$) or a manganese salt.

The solvent is a hydrophilic solvent or a hydrophobic solvent, and a mass ratio of the mixture of the PLAN and the manganese compound to the solvent is between 0.1:1 and 0.5:1.

The particle size of the manganese compound is between 8 nm and 100 μm. The manganese compound is sieved using a sieve having a mesh of 200-400 mesh, preferably, 300 mesh.

Preferably, the dopant can be further added to a mixture of the thermally-oxidized polyacrylonitrile and the manganese compound, and the mixing is achieved by stirring, ultrasound, or ball milling. The further doping can provide better coating effect and compatibility at the molecular level.

(4) Drying the polyacrylonitrile coated manganese compound in an oven at a temperature of between 200 and 250°

C. for between 1 and 10 hrs until the solvent is evaporated completely and the polyacrylonitrile coated on the manganese compound is crosslinked to form a solid, to yield a carbonized precursor coated manganese compound. Preferably, the drying time is 3 hours. The carbonized precursor coated manganese compound can be ground to be powders.

(5) Calcining the carbonized precursor coated manganese compound in the presence of an inert gas flow of between 10 and 500 mL/min for between 1 and 10 hrs at a temperature of between 500 and 900° C., to yield a carbon-coated manganous oxide. Preferably, the calcination temperature is 700° C. and the time lasts 4 hours.

Preferably, the inert gas is nitrogen or argon.

The invention also provides a carbon-coated manganous oxide prepared according to the above-mentioned method.

Example 1

Figure 3:
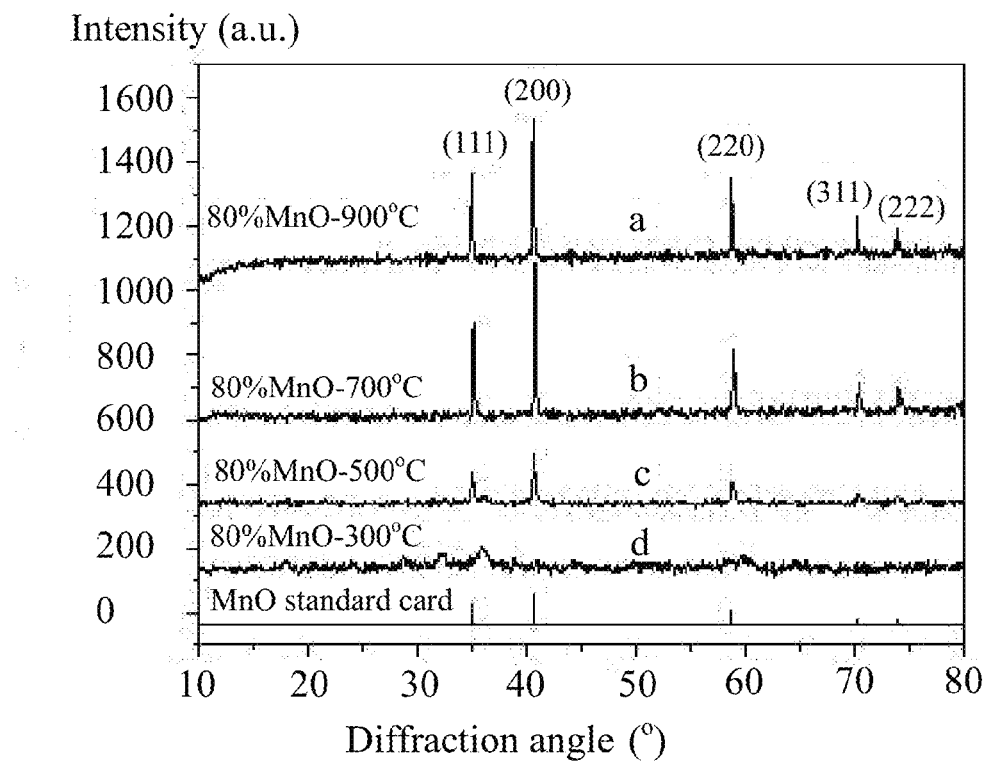
FIG. 3 is an XRD pattern of a product prepared in Example 1, where the product is carbon-coated manganous oxide.

4 g of liquid polyacrylonitrile (LPAN) solution (molecular weight 4000) were stirred at 120° C. for 120 hrs, to yield a cyclized polyacrylonitrile solution. The cyclized LPAN solution was heated at 300° C. for 8 hrs to yield a thermally-oxidized polyacrylonitrile (OPAN) comprising a ladder structure. The thermally-oxidized polyacrylonitrile was mixed with 10 g of manganese dioxide and 20 mL of a solvent. The resulting mixture was ball milled using a planetary type ball mill for 10 hrs (400 rad/min), and the ratio of grinding media to material was 7:1. Thereafter, a product was collected and dried in an oven at 220° C. for 3 hrs to yield a thermally-oxidized precursor (low temperature carbonization precursor-coated manganese compound). The thermally-oxidized precursor was calcined in a ceramic boat in the presence of a nitrogen gas flow of 150 mL/min for 4 hrs at the temperature of between 500 and 900° C., and then was cooled to room temperature, to yield carbon-coated manganous oxide. The morphologies of the product at the calcination temperature of 300° C., 500° C., 700° C. and 900° C. are shown in FIGS. 1A, 1B, 1C and 1D, respectively. The product comprises 80 wt. % of MnO (the material is manganese dioxide, and the product is manganous oxide). The XRD pattern thereof is shown in FIG. 3.

Example 2

Figure 2A:
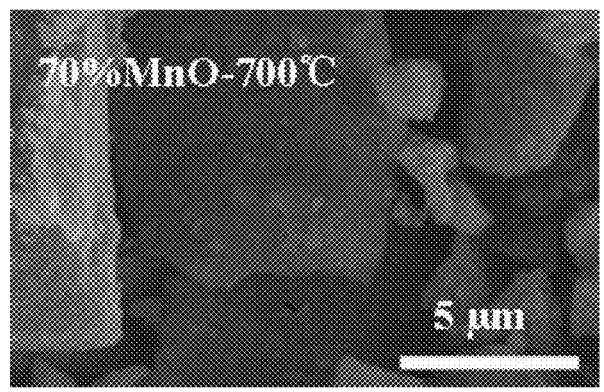
FIG. 2A is a SEM pattern of a product prepared in Example 2, where the product is carbon-coated manganous oxide.
Figure 4:
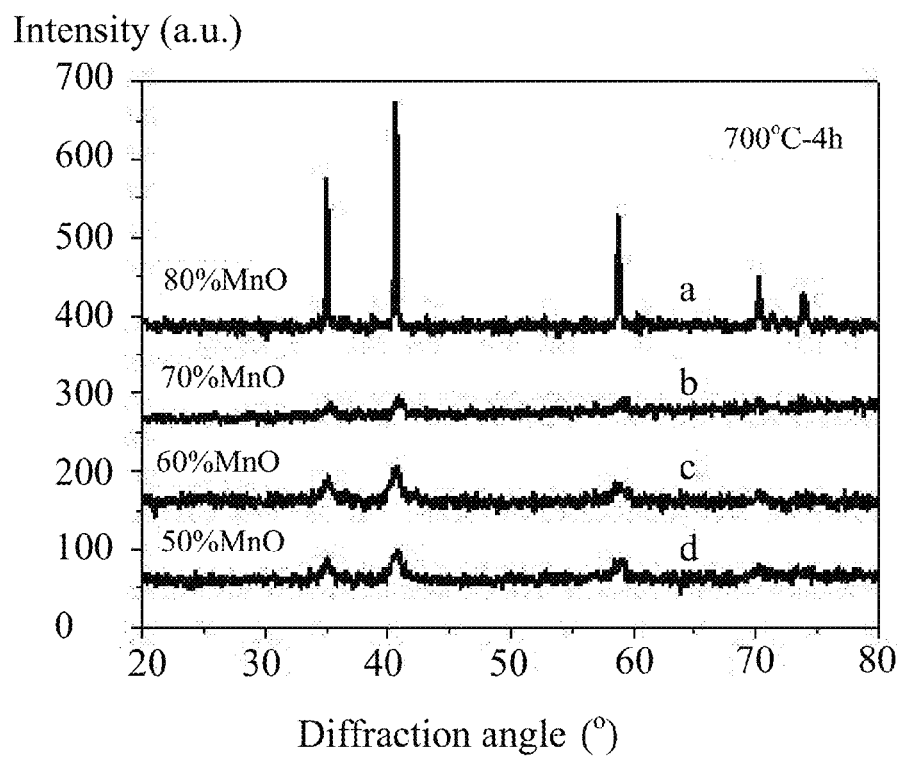
FIG. 4 is an XRD pattern of products having different weight percentages of manganese.

6 g of liquid polyacrylonitrile (LPAN) solution (molecular weight 4000) were stirred at 120° C. for 120 hrs, to yield a cyclized solution. The cyclized solution was heated at 200° C. for 8 hrs to yield a thermally-oxidized polyacrylonitrile (OPAN) comprising a ladder structure. The thermally-oxidized polyacrylonitrile (OPAN) was mixed with 11.25 g of manganese dioxide and 20 mL of a solvent. The resulting mixture was ball milled using a planetary type ball mill for 10 hrs (400 rad/min), and the ratio of grinding media to material was 15:1. Thereafter, a product was collected and dried in an oven at 250° C. for 3 hrs to yield a thermally-oxidized precursor. The thermally-oxidized precursor was calcined in a ceramic boat in the presence of a nitrogen gas flow of 150 mL/min for 4 hrs at the temperature of 700° C., and then was cooled to room temperature, to yield a mixture of carbon-coated manganous oxide. The product comprises 70 wt. % of MnO. The morphology thereof is shown in FIG. 2A. The XRD pattern thereof is shown in FIG. 4.

Example 3

Figure 2B:
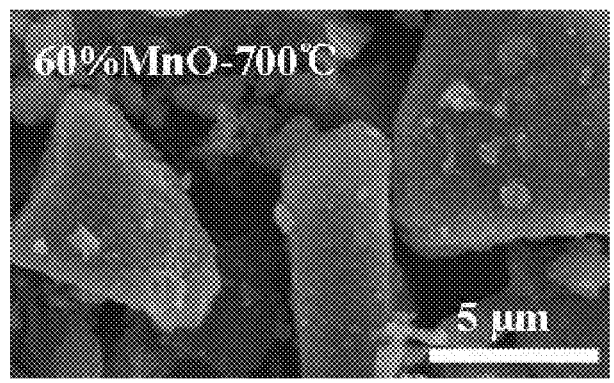
FIG. 2B is a SEM pattern of a product prepared in Example 3, where the product is carbon-coated manganous oxide.

8 g of liquid polyacrylonitrile (LPAN) solution (molecular weight 4000) were stirred at 120° C. for 120 hrs to yield a cyclized solution. The cyclized solution was heated at 250° C. for 8 hrs to yield a thermally-oxidized polyacrylonitrile (OPAN) comprising a ladder structure. The thermally-oxidized polyacrylonitrile (OPAN) was mixed with 7.5 g of manganese dioxide and 20 mL of a solvent. The resulting mixture was ball milled using a planetary type ball mill for 10 hrs (400 rad/min), and the ratio of grinding media to material was 7:1. Thereafter, a product was collected and dried in an oven at 280° C. for 3 hrs, to yield a thermally-oxidized precursor. The thermally-oxidized precursor was calcined in a ceramic boat in the presence of an argon gas flow of 150 mL/min for 4 hrs at the temperature of 700° C., and then was cooled to room temperature, to yield a mixture of carbon-coated manganous oxide. The product comprises 60 wt. % of MnO. The morphology thereof is shown in FIG. 2B. The XRD pattern thereof is shown in FIG. 4.

Example 4

Figure 2C:
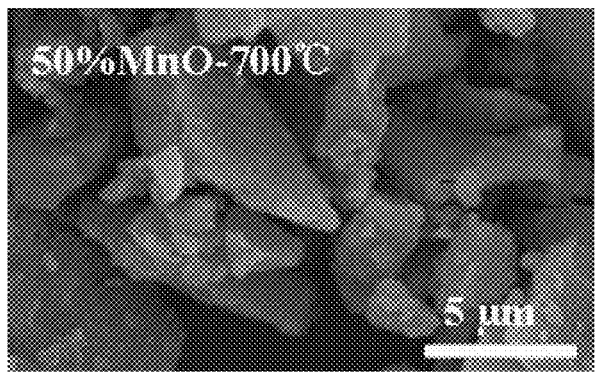
FIG. 2C is a SEM pattern of a product prepared in Example 4, where the product is carbon-coated manganous oxide.

10 g of liquid polyacrylonitrile (LPAN) solution (molecular weight 4000) were stirred at 120° C. for 120 hrs to yield a cyclized solution. The cyclized solution was heated at between 200 and 300° C. for 8 hrs to yield a thermally-oxidized polyacrylonitrile (OPAN) comprising a ladder structure. The thermally-oxidized polyacrylonitrile (OPAN) was mixed with 6.25 g of manganese dioxide and 20 mL of a solvent. The resulting mixture was ball milled using a planetary type ball mill for 10 hrs (400 rad/min), and the ratio of grinding media to material was 7:1. Thereafter, a product was collected and dried in an oven at 220° C. for 3 hrs, to yield a thermally-oxidized precursor. The thermally-oxidized precursor was calcined in a ceramic boat in the presence of an argon gas flow of 150 mL/min for 4 hrs at the temperature of 700° C., and then was cooled to room temperature, to yield a mixture of carbon-coated manganous oxide. The product comprises 50 wt. % of MnO. The morphology thereof is shown in FIG. 2C. The XRD pattern thereof is shown in FIG. 4.

Figure 5:
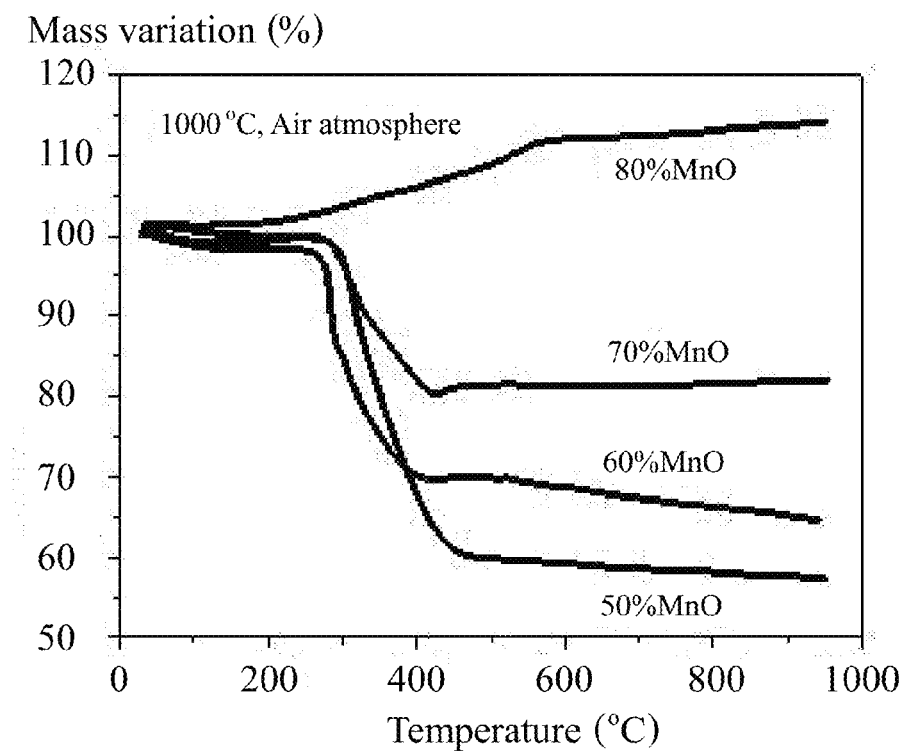
FIG. 5 is a thermogravimetric analysis graph of carbon-coated manganous oxide products having different manganous contents in the air atmosphere.

FIG. 5 is a thermogravimetric analysis graph of carbon-coated manganous oxide products having different manganous contents in the air atmosphere.

Figure 6:
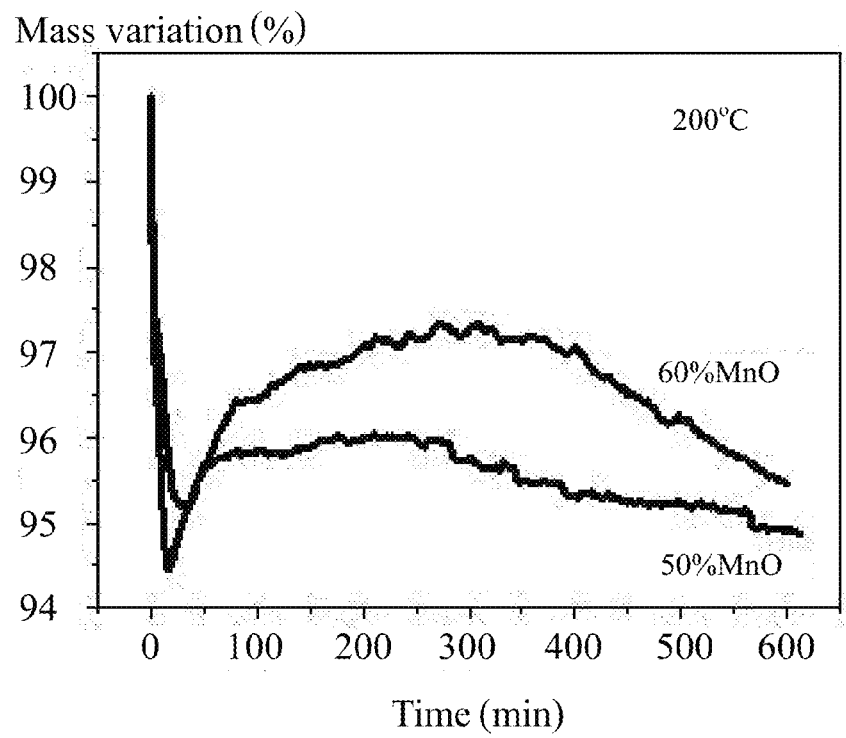
FIG. 6 is a thermogravimetric analysis graph of carbon-coated manganous oxide products comprising 50 wt. % and 60 wt. % of MnO, respectively, in the air atmosphere at a constant temperature for 10 hours.

FIG. 6 is a thermogravimetric analysis graph of carbon-coated manganous oxide products comprising 50 wt. % and 60 wt. % of MnO, respectively, in the air atmosphere at a constant temperature for 10 hours.

The obtained carbon-coated manganous oxide has good compatibility with carbon source and the carbon membrane is porous, so that the release speed of manganous oxide can be effectively controlled, which is favorable for the carbon-coated manganous oxide to be used as an antifouling additive for marine antifouling paints. In addition, the outer coating of polyacrylonitrile can prevent the oxidation of manganous oxide, and the manganous oxide are slowly released to the surface of the coating via the porous coating, which increases the contact area of the adsorbate and catalyst, and improves the catalytic performance.

The method of the invention involves a simple process and low production costs, and the resulting carbon-coated manganous oxide has high purity, high yield, uniform distribution of particle sizes, and good morphology. The LPAN solution contains multiple functional groups, and as a liquid precursor, after being modified using a dopant, the LPAN can uniformly mix with and bind to the dopant.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of preparing carbon-coated manganous oxide, the method comprising:
    (1) preparing a liquid polyacrylonitrile (LPAN) solution as a carbon source, stiffing the LPAN solution at a temperature of between 100 and 200° C. for between 100 and 200 hrs to yield a cyclized polyacrylonitrile solution;
    (2) heating the cyclized LPAN solution at between 200 and 300° C. for between 1 and 10 hrs to yield a thermally-oxidized polyacrylonitrile (OPAN) comprising a ladder structure;
    (3) mixing the thermally-oxidized polyacrylonitrile with a manganese compound with a mass ratio thereof being between 0.1:1 and 0.9:1, to yield a mixture, and adding a solvent to the mixture and uniformly mixing, to yield a polyacrylonitrile coated manganese compound;
    (4) drying the polyacrylonitrile coated manganese compound in an oven at a temperature of between 200 and 250° C. for between 1 and 10 hrs until the solvent is evaporated completely and the polyacrylonitrile coated on the manganese compound is crosslinked to form a solid, to yield a carbonized precursor coated manganese compound; and
    (5) calcining the carbonized precursor coated manganese compound in the presence of an inert gas flow of between 10 and 500 mL/min for between 1 and 10 hrs at a temperature of between 500 and 900° C., to yield a carbon-coated manganous oxide.

2. The method of claim 1, wherein in 1), a dopant is added to and uniformly mixed with the cyclized LPAN solution.

3. The method of claim 2, wherein a mass ratio of the dopant to the LPAN solution is between 0.01:1 and 0.5:1.

4. The method of claim 2, wherein the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, organometallic compound, or a mixture thereof; and the non-metallic dopant is silicon, phosphorus, boron, nitrogen, carbon, sulfur, or a compound thereof, or a mixture thereof.

5. The method of claim 1, wherein the liquid polyacrylonitrile (LPAN) solution employs liquid polyacrylonitrile as a solute and contains no solvent, and the LPAN has a relative molecular weight of between 106 and 100000.

6. The method of claim 5, wherein the PLAN is a homopolymer of acrylonitrile, or a copolymer of acrylonitrile and a vinyl monomer.

7. The method of claim 6, wherein the vinyl monomer is selected from the group of styrene, methyl methacrylate, hydroxyethyl methylacrylate, acrylic acid, itaconic acid.

8. The method of claim 1, wherein in 3), the uniform mixing of the mixture and the solvent is achieved by stiffing, ultrasound, or ball milling.

9. The method of claim 1, wherein in 3), the manganese compound is manganese dioxide ($MnO_2$) or a manganese salt.

* * * * *